| United States Patent [19] | [11] Patent Number: 4,962,241 |
| Yasuda et al. | [45] Date of Patent: Oct. 9, 1990 |

[54] PROCESS FOR PRODUCING DIHYDROXYNAPHTHALENES

[75] Inventors: Masaaki Yasuda; Hisaya Miki, both of Iwakuni, Japan

[73] Assignee: Mitsui Petrochemical Industries, Ltd., Tokyo, Japan

[21] Appl. No.: 309,671

[22] PCT Filed: Jun. 9, 1988

[86] PCT No.: PCT/JP88/00555

§ 371 Date: Feb. 3, 1989

§ 102(e) Date: Feb. 3, 1989

[87] PCT Pub. No.: WO88/09781

PCT Pub. Date: Dec. 15, 1988

[30] Foreign Application Priority Data

Jun. 12, 1987 [JP] Japan .................................. 62-146445

[51] Int. Cl.$^5$ ............................................. C07C 39/38
[52] U.S. Cl. .................................. 568/737; 568/716; 568/731; 568/735; 568/741
[58] Field of Search ............... 568/737, 741, 716, 731, 568/735

[56] References Cited

U.S. PATENT DOCUMENTS

| 4,171,458 | 10/1979 | Schuster et al. | 568/735 |
| 4,171,459 | 10/1979 | Schuster et al. | 568/735 |
| 4,783,557 | 11/1988 | Haneda et al. | 568/741 |

FOREIGN PATENT DOCUMENTS

| 1024531 | 2/1986 | Japan | 568/737 |
| 61-282333 | 12/1986 | Japan | 568/715 |
| 62-70339 | 3/1987 | Japan . | |
| 2176188 | 12/1986 | United Kingdom | 568/741 |

OTHER PUBLICATIONS

Chemical Abstracts, vol. 109, 23057t (1988).

*Primary Examiner*—Werren B. Lone
*Attorney, Agent, or Firm*—Sherman and Shalloway

[57] ABSTRACT

The process of the present invention for producing dihydroxynaphthalenes comprises hydrolyzing a diacyloxynaphthalene in a water-containing solvent in the presence of an acid catalyst. The use of an acid as a hydrolyzing catalyst enables dihydroxynaphthalenes to be obtained with high purity and in high yield.

17 Claims, No Drawings

PROCESS FOR PRODUCING DIHYDROXYNAPHTHALENES

TECHNICAL FIELD

The present invention relates to a process for producing hydroxynaphthalenes useful as starting materials for the production of synthetic resins, synthetic fibers, pharmaceuticals, agrichemicals, dyes, etc. More particularly, the present invention relates to a process for producing hydroxymophthalenes of high purity.

BACKGROUND ART 2,6-Dihydroxynaphthalene is a compound useful as a starting material for the production of synthectic resins, synthetic fibers, pharmaceuticals, agrichemicals, dyes, etc.

A classical method for the production of 2,6-dihydroxynaphthalene consists of subjecting 2-naphthol-6-sulfonic acid to alkali fusion with potassium hydroxide. This method, however, has the problems of low yield and difficult separation from the tar content. Furthermore, the end compound 2,6-dihydroynaphthalene is prone to crystallization and the inorganic salt used in a large amount as a reactant tends to be incorporated in the crystal of 2,6-dihydroxynaphthaelen, making it difficult to be obtained with high purity.

It is also known that 2,6-dihydroxynaphthalene can be produced by first oxidizing 2,6-diisopropylnaphthalene with molecular oxygen in the presence of a base to form diisopropylnaphthalene dihydroperoxide, then acid-decomposing this peroxide with an acidic catalyst such as sulfuric acid. A problem with this method is that when 2,6-diisopropylnaphthalene is oxidized with molecular oxygen in the presence of a base, not only is the end compound 2,6-diisopropylnaphthalene dihydroperoxide (hereinafter sometimes abbreviated as DHP) obtained but also various by-products are formed in large quantities. Among these by-products are carbinols such as 2-(2-hydroxy-2-propyl-6-(2-hydroperoxy-2-propyl)naphthalene (hereinafter sometimes abbreviated as HHP), 2,6-bis(2-hydroxy-2-propyl)naphthalene (hereinafter sometimes abbreviated as DCA) and 2-isopropyl-6-(2-hydroxy-2propyl)naphthalene (hereinafter sometimes abbreviated as MCA), and monohydroperoxides such as 2-isopropyl-6-(2-hydroperoxy-2-propyl)naphthalene (hereinafter sometimes abbreviated as MHP). Furthermore, when the reaction product obtained by oxidation of 2,6-diisopropylnaphthalene and which contains not only DHP but also various by-products is subjected to acid decomposition in the presence of an acid catalyst such as sulfuric acid, the end compound dihydroxynaphthalene is obtained together with various products of acid decomposition reaction such as isopropylnaphthol.

As described above, if 2,6-diisopropylnaphthalene is oxidized to DHP by reaction with molecular oxygen in the presence of a base and if the resulting DHP is subjected to acid decomposition with an acidic catalyst such as sulfuric acid, the reaction mixture obtained will contain not only the desired dihydroxynaphthalene but also large amounts of various by-products of the reaction.

It is known that 2,6-dihydroxynaphthalene can be purified by recrystallization using solvents such as alcohol, ether, acetone, acetic acid, benzene and water. However, none of these solvents are completely satisfactory for recrystallization purposes because their ability to dissolve 2,6-dihydroxynaphthalene is either too high or too low to attain good results.

Under these circumstances, other purification methods have been reviewed. In one method, cumeme or some other suitable material is added to the reaction product of acid decomposition or, in some instances, the concentrate obtained by removing the solvent and other materials that have been employed in the reaction of acid decomposition, and the resulting precipitate of crude 2,6-dihydroxynaphthalene is sublimated to obtain pure 2,6-dihydroxynaphthalene. Another method comprises using an aqueous alcohol or hydrous ketone as a solvent for recrystallization. Use of activated carbon for decolorizing purposes has also been reviewed. However, these methods have suffered the problem that satisfactory values of purity cannot be attained if an attempt is made to increase the recovery rate and that the decoloring effect is not high enough for practical purposes.

DISCLOSURE OF INVENTION

The present inventors conducted intensive studies with a view to solving the aforementioned problems of the prior art. As a result, the present inventors found that a hydroxynaphthalene, in particular dihydroxynaphthalene, could be obtained with high purity by hydrolyzing diacyloxynaphthalene in the presence of an acid catalyst. The present invention has been accomplished on the basis of this finding the diacyloxynaphthalene may be obtained by first decomposing diisopropylnaphthalene dihydroperoxide with an acid, then reacting the resulting dihydroxynaphthalene-containing reaction mixture of acid decomposition with an acyloxylating agent in the presence of a catalyst.

The principal object of the present invention which aims at solving the aforementioned problems is to provide a process for producing a hydroxynaphthalene by which a hydroxynaphthalene, in particular dihydroxynaphthalene, can be produced from diacyloxynaphthalene both in high yield and with high purity.

The process of the present invention for producing dihydroxynaphthalene is characterized by hydrolyzing diacyloxynaphthalene in a water-containing solvent in the presence of an acid catalyst to form dihydroxynaphthalene and then separating this dihydroxynaphthalene from the reaction mixture.

In accordance with the process of the present invention for producing dihydroxynaphthalene, a hydroxynaphthalene is obtained by hydrolyzing diacyloxynaphthalene in a water-containing solvent in the presence of an acid catalyst, so a hydroxynaphthalene, in particular dihydroxynaphthalene, of high purity can be produced in high yield.

BEST MODE FOR CARRYING OUT THE INVENTION

The process of the present invention for producing dihydroxynaphthalene is described hereinafter in a specific way.

In the present invention, dihydroxynaphthalene is produced by hydrolyzing diacyloxynaphthalene in a water-containing solvent in the presence of an acid catalyst Each of the acyloxy groups in the diacyloxynaphthalene as the starting material in the present invention is represented by the following general formula:

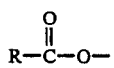

(where R is a lower alkyl group or an aryl group). Specific examples of the acyloxy group include formyloxy, acetoxy, propionyloxy, butyryloxy, valeryloxy, benzoyloxy and tobuyloxy, with acetoxy being preferred.

The hydroxynaphthalene to be produced by the present invention is preferably dihydroxynaphthalene, with 2,6-di hydroxynaphthalene being particularly preferred.

Also included within the scope of the hydroxynaphthalene to be produced in the present invention are 2,4-dihydroxynaphthalene and 2,7-dihydroxynaphthalene. The term "acyloxynaphthalene" or "hydroxynaphthalene" as used herein includes acyloxyhydroxynaphthalene in which one of the two acyloxy groups in the diacyloxynaphthalene is hydrolyzed, with the other remaining as it is.

Examples of the acid catalysts that can be used to hydrolyze diacyloxynaphthalene include:
inorganic acids such as sulfuric acid, hydrochloric acid, perchloric acid and hydrofluoric acid; strong acidic ion-exchange resins; solid acids such as silica and silica alumina; organic acids such as chloroacetic acid, methanesulfonic acid, benzenesulfonic acid and toluenesulfonic acid; and Lewis acids such as boron fluoride and zinc chloride.

These acid catalysts are used in amounts of 0.05–10 wt %, preferably 0.2–1.0 wt %, of the reaction solvent.

The above-described reaction for hydrolysis of diacyloxynaphthalene is performed using a solvent, and it is particularly preferable to use a solvent that is highly miscible with water, desirably forming a homogeneous system, under the reaction conditions employed. Suitable solvents are alcohols such as methanol, ethanol, isopropanol and ethylene glycol, carboxylic acids such as formic acid, acetic acid and propionic acid, ketones such as acetone and methyl ethly ketone, ethers such as dioxanecarbitol, and nitriles such as acetonitrile.

The amount of water that is necessary to hydrolyze the diacyloxynaphthalene may be defined as follows. If an alcohol is used as the solvent, not only the reaction of hydrolysis but also the reaction of ester exchange occurs so the amount of water relative to diacyloxynaphthalene is preferably no greater than 2.0 in molar ratio. However, if solvents other than alcohols are used, water is used in a molar ratio to diacyloxynaphthalene of at least 2.0, preferably at least 5.0, more preferably at least 10.0.

In carrying out the above-described reaction for hydrolysis of diacyloxynaphthalene, the solvent is used in an amount of 3–5 parts by weight, preferably 5–10 parts by weight, per part by weight of diacyloxynaphthalene. The solvent is used in such an amount that not only the diacyloxynaphthalene but also the hydroxynaphthalene produced dissolves completely in the solvent. However, so long as the diacyloxynaphthalene and hydroxynaphthalene are dissolved in the solvent used, the amount of the solvent used is preferably decreased so that the concentration of the resulting hydroxynaphthalene in the solvent will be increased.

If the reaction is performed at atmospheric pressure, the reaction temperature is limited by the boiling point of the solvent used but is normally in the range of 40°–200° C., preferably 60°–100° C.

The reaction time normally ranges from 30 minutes to 10 hours and the reaction is substantially completed in about 5 hours. If dihydroxynaphthalene is to be obtained as the reaction product, the end point of the reaction can be approximated by the time when monoacyloxynaphthalene in which one of the two acyloxy groups in the diacyloxynaphthalene remains is no longer detectable. If the reaction time is unduly long, a dimer of dihydroxynaphthalene will form although its amount is small. Besides, other by-products will also be generated.

In the reaction of hydrolysis of esters, the catalyst may generally be either an acid or a base. However, if an acid is used, it serves not only as a catalyst for the reaction of hydrolysis but also as a catalyst for the reaction of esterification. Therefore, a base is normally used as a catalyst. In fact, J. Chem. Soc., 35, 1943 describes that purified 2,6-dihydroxynaphthalene is obtained by a process comprising obtaining 2,6-dihydroxynaphthalene by alkali fusion of sodium 2-hydroxy-6-sulfonate, converting the dihydroxynaphthalene to 2,6-diacetoxynaphthalene, hydrolyzing it with an aqueous alkali in a nitrogen atmosphere and recrystallizing the hydrolyzate with an excess amount of water.

However, if a solution of a hydroxynaphthalene, in particular 2,6-dihydroxynaphthalene, in aqueous sodium hydroxide is left in the air, it gradually assumes a color with time until it becomes black. As is evidenced by this fact, 2,6-dihydroxynaphthalene is very unstable in alkali solutions. The present inventors conducted an investigation to locate the reason for the coloring of the alkali solution of 2,6-hydroxynaphthalene, and found that the product contained 2,2',6,6'-tetrahydroxy-1,1'-binaphthyl which is a dimer of 2,6-dihydroxynaphthalene. Since this dimer is a white crystal, the coloring matter is assumed to be a higher condensate of this dimer. The formation of the dimer as a by-product is observed even in a nitrogen atmosphere under alkaline conditions. Since this dimer is a solid having a decomposition temperature of 318°–320° C., it is not easily separable from 2,6-dihydroxynaphthalene (m.p. 220.9°–222° C.). Therefore, in order to obtain purified 2,6-dihydroxynaphthalene, the starting material preferably contains the least amount of this dimer. In other words, if a hydroxynaphthalene, especially 2,6-dihydroxynaphthalene, is to be obtained by hydrolysis of diacetoxynaphthalene, the condition for hydrolysis must be such that the formation of the by-product dimer is negligible.

However, according to the finding of the present inventors, the formation of the dimer as a by-product is unavoidable if diacetoxynaphthalene is hydrolyzed in the presence of an alkali catalyst.

In the present invention, a dihydroxynaphthalene is produced from diacyloxynaphthalene using an acid as a catalyst for the hydrolysis of diacyloxynaphthalene, so the resulting dihydroxynaphthalene can be purified by merely washing it with a solvent.

In the present invention, a dihydroxynaphthalene is produced by the reaction of hydrolysis of diacyloxynaphthalene. The diacyloxynaphthalene used as the starting material may be prepared by any method. Preferably, it is prepared by the following method: diisopropylnaphthalene is oxidized with molecular oxygen in the presence of a base; the resulting product of oxidation reaction containing diisopropylnaphthalene dihydroperoxide is decomposed with an acid to obtain the reaction product of acid decomposition containing dihydroxynaphthalene; an acyloxylating agent is added to this reaction product to effect reaction between the acyloxylating agent and the dihydroxynaphthalene; and the resulting diacyloxynaphthalene is separated from the reaction mixture.

This preferred method of preparing the diacyloxynaphthalene is described below in a more specific way.

First, diisopropylnaphthalene is oxidized with molecular oxygen in the presence of a base to form diisopropylnaphthalene dihydroperoxide, and the product of oxidation reaction which contains the so formed diisopropylnaphthalene dihydroperoxide is subjected to acid decomposition with an acid catalyst such as sulfuric acid, thereby preparing the dihydroxynaphthalene-containing product of acid decomposition.

Specific examples of the diisopropylnaphthalene include 2,6-diisopropylnaphthalene, 2,7-diisopropylnaphthalene and 1,4-diisopropylnaphthalene, among which 2,6-diisopropylnaphthalene is preferred.

As described above, diisopropylnaphthalene is oxidized and subsequently decomposed with an acid to produce the dihydroxynaphthalene-containing reaction product of acid decomposition. The solvent, acid catalyst and other reaction conditions employed for this purpose can be varied over a broad range.

OXIDATION REACTION

A preferred embodiment of the production of the dihydroxynaphthalene-containing reaction product of acid decomposition from diisopropylnaphthalene is described below in detail.

The oxidation reaction of diisopropylnaphthalene is performed by adding diisopropylnaphthalene to an aqueous solution of a base, mixing them mechanically to form an emulsion, and bubbling the emulsion with a gas containing molecular oxygen.

An alkali metal compound is preferably used as the base. Specific examples of the alkali metal compound include sodium hydroxide, potassium hydroxide, sodium carbonate and potassium carbonate. The concentration of the alkali metal compound in aqueous solution is preferably not more than 20wt %. It is normally preferable for the aqueous base solution to be used in the reaction mixture in such an amount that it accounts for 5-80 wt % of the reaction mixture, with the range of 20-70 wt % being particularly preferred. If the aqueous base solution is used in the amount of less than 5 wt % of the reaction mixture, neither the oily unreacted diisopropylnaphthalene nor its oxidation product will be dispersed satisfactorily in the reaction liquor made of the aqueous base solution and only an incomplete emulsion will form to cause adverse effects on the oxidation reaction. If the aqueous base solution is used in an amount exceeding 80 wt % of the reaction mixture, the reaction system also fails to provide a satisfactory emulsion. In the oxidation reaction, the pH of the aqueous base solution is normally held in the range of 7-14, preferably 11-14.

Diisopropylnaphthalene and its oxidation product can be normally emulsified in the aqueous base solution to a satisfactory degree by mechanical agitation but, if desired, agitation may be effected in the presence of a known emulsifier such as stearic acid.

Other useful examples of the base are alkaline earth metal hydroxides such as calcium hydroxide, magnesium hydroxide and strontium hydroxide. Calcium hydrixide is particularly preferred. These alkaline earth metal hydroxides may be used either independently or in combination with the aforementioned alkali metal compounds.

Oxygen gas may be used independently as the molecular oxygen but normally the air suffices for producing good results. The required amount of molecular oxygen is not limited to any particular value but it normally is in the range of 5-15 Nl/h in terms of oxygen gas per 100 g of the diisopropylnaphthalene charged for oxidation reaction.

The reaction temperature normally ranges from 80° to 150° C., preferably from 90° to 130° C. The reaction time which varies with the reaction temperature and other reaction conditions is normally in the range of 6-40 hours. The degree of conversion of diisopropylnaphthalene is preferably at least 80% in order to increase the yield of dihydroperoxide. The reaction is normally carried out at atmospheric pressure but may be performed under superatmospheric or subatmospheric pressure as required.

In the above-described oxidation reaction of diisopropylnaphthalene a reaction initiator is preferably employed in addition to a catalyst. For example, besides the reaction mixture of autoxidation of 2,6-diisopropylnaphthalene, α,α'-azobis(cyclohexane-1-carbonitrile) may be used as a reaction initiator. The induction period of the reaction can be shortened by using a reaction initiator. The reaction initiator is normally used in an amount ranging from 0.005 to 1 part by weight per 100 parts by weight of the charged reaction mixture containing the starting diisopropylnaphthalene.

A catalyst may be employed in the oxidation reaction and preferred examples of the catalyst are copper, cobalt salt and palladium. These catalysts are normally used in amount ranging from 0.5 ppm to 1,000 ppm.

By performing the oxidation reaction of diisopropylnaphthalene in the manner described above, not only diisopropylnaphthalene dihydroperoxide (DHP) but also various by-products are formed. The by-products include carbinols such as(2-hydroxy-2-propyl)-(2-hydroperoxy-2-propyl)naphthalene (HHP), bis(2-hydroxy-2-propyl)naphthalene (DCA) and isopropyl(2-hydroxy-2propyl)naphthalene (MCA), and monohydroperoxides such as isopropyl(2-hydroperoxy-2-propyl)naphthalene (MHP).

The composition of the reaction product resulting from the above-described oxidation reaction can be determined by the following procedures: after the reaction, the organic phase is separated from the aqueous phase; the aqueous phase is extracted with ether; and the organic phase and the ether extract are analyzed by liquid chromatography to determine the quantities of the unreacted diisopropylnaphthalene and the products of oxidation reaction such as DHP, HHP, DCA, MHP and MCA.

The oxidation reaction of diisopropylnaphthalene is preferably performed to attain a conversion of at least 80% and the resulting reaction mixture containing the unreacted diisopropylnaphthalene, diisopropylnaphthalene dihydroperoxide and various by-products is subjected to the subsequent step of acid decomposition. Normally, a suitable organic solvent such as methyl isobutyl ketone (MIBK) is added in an appropriate amount to the above-described oxidation reaction mixture and the organic phase containing this reaction mixture is separated from the aqueous phase and subjected to subsequent acid decomposition. In the following description, this organic phase is sometimes referred to as the starting material for acid decomposition.

REACTION OF ACID DECOMPOSITION

Using the thus obtained starting material for acid decomposition, the diisopropylnaphthalene dihydroperoxide present in it is acid-decomposed in the presence of an acidic catalyst so as to produce the dihydroxynaphthalene-containing reaction product of acid decomposition. The starting material for acid decomposition contains the aforementioned carbinols that were formed as by-products in the previous step of oxidation reaction, so if necessary, hydrogen peroxide may also be employed in the reaction of acid decomposition in order to ensure that HHP and DCA among the by-products carbinols are oxidized to dihydroperoxides, which are acid-decomposed with an acidic catalyst together with the diisopropylnaphthalene dihydroperoxide. This method is preferable for the purpose of obtaining the desired dihydroxynaphthalene in high yield.

If the degree of conversion of diisopropylnaphthalene is increased to 80% and above not only the yield of DHP but also those of HHP and DCA are increased. If hydrogen peroxide is employed in the reaction of acid decomposition, HHP and DCA are converted into DHP, thereby enabling the desired dihydroxynaphthalene to be obtained in high yield. The use of hydrogen peroxide is also preferable for the reason that the yield of MHP which does not contribute to the formation of dihydroxynaphthalene can be reduced. The yield of dihydroxynaphthalene can be further increased by ensuring that the degree of conversion of diisopropylnaphthalene is at least 90%, more preferably at least 95%.

The hydrogen peroxide used for this purpose may be anhydrous hydrogen peroxide or a solution thereof in water. Materials that generate hydrogen peroxide under the reaction conditions employed, such as sodium peroxide and calcium peroxide, may also be employed but it is preferable to use an aqueous solution of hydrogen peroxide. In particular, the desired dihydroxynaphthalene can be obtained in high yield by performing the reaction of acid decomposition using 0.9-2 moles, preferably 1.0-1.5 moles, of hydrogen peroxide per mole of the alcoholic hydroxyl group in the carbinols described above. Using hydrogen peroxide under this condition is preferable since it also inhibits markedly the formation of by-products due to the condensation of carbinols.

Preferred examples of the acidic catalyst that can be used in the reaction of acid decomposition include: inorganic acids such as sulfuric acid, hydrochloric acid, hydrogen fluoride and phosphoric acid; solid acids such as strong acidic ion-exchange resins, silica gel and silica alumina; organic acids such as chloroacetic acid, methanesulfonic acid, benzenesulfonic acid and toluenesulfonic acid; and heteropolyacids such as phosphotungstic acid and phosphomolybdic acid. These acidic catalysts may be added per se to the reaction system; alternatively, if these acidic catalysts are soluble in a certain solvent, they may be added to the reaction system as solutions in appropriate inert solvents. The amount of the acidic catalysts used varies with their type and the reaction conditions employed, and it normally is within the range of 0.01-10 wt % of the total reaction mixture.

As already mentioned, it is advantageous for practical purposes that after the reaction for the oxidation of diisopropylnaphthalene, the obtained diisopropylnaphthalene dihydroperoxide and by-products are transferred from the reaction mixture into an organic solvent such as methyl isobutyl ketone, with the reaction of acid decomposition being subsequently performed using this organic solvent as the reaction solvent. However, the reaction solvent is by no means limited to methyl isobutyl ketone and other inert organic solvents may be used as required, such as ketones (e.g.,acetone and methyl ethyl ketone), alcohols (e.g., methanol and ethanol), lower aliphatic carboxylic acids (e.g. acetic acid and propionic acid), hydrocarbons (e.g., benzene, toluene, xylene, hexane and heptane), nitriles (e.g., acetonitrile), phenols (e.g., phenol and cresol) and nitro compounds (e.g., nitromethane and nitrobenzene). Mixtures of these solvents may also be used. Using carboxylic acids as reaction solvents is advantageous for the purpose of acyloxylating the dihydroperoxide with an acyloxylating agent (see below) either simultaneously with or subsequent to the step of acid decomposition.

The reaction of acid decomposition is carried out at a temperature in the range of 0°-100° C., preferably 20°-80° C.

The reaction product of acid decomposition thus obtained in the present invention contains not only the desired dihydroxynaphthalene but also by-product impurities including isopropylnaphthol, acetylnaphthol, dihydroxynaphthalene dimer and tar, as well the by-product acetone and the reaction solvents such as methyl isobutyl ketone and cumene that have been used in the step of acid decomposition. The mixture which is to be subjected to acyloxylation reaction as described below normally contains dihydroxynaphthalene in a proportion ranging from 5 to 30 wt %. The proportion of the reaction product of acid decomposition (i.e., the mixture minus the by-product acetone and the reaction solvent) that is occupied by dihydroxynaphthalene is normally in the range of 40–80 wt % and in the present invention the above-characterized reaction mixture of acid decomposition is preferably subjected to acyloxylation reaction with an acyloxylating agent as described below.

DIACYLOXYNAPHTHALENE

An acyloxylating agent is added to the thus obtained dihydroxynaphthalene-containing reaction mixture of acid decomposition, and the dihydroxynaphthalene is reacted with the acyloxylating agent in the presence of a catalyst to produce the desired diacyloxynaphthalene. In performing the acyloxylation reaction, low-boiling point substances such as the by-product acetone and the reaction solvent employed may optionally be removed in appropriate amounts from the reaction mixture of acid decomposition by a suitable method such as distillation.

The acyloxylating agent is preferably added in an amount of 1-20 moles, preferably 2-5 moles, per mole of the dihydroxynaphthalene in the reaction product of acid decomposition.

The acyloxylating agent used in the present invention may be exemplified by lower aliphatic carboxylic acids such as formic acid, acetic acid, propionic acid, butyric acid and valeric acid, aromatic carboxylic acids such as benzoic acid and toluic acid, and acid chlorides such as acetyl chloride, all being in the anhydrous form.

The catalyst for use in the reaction between the dihydroxynaphthalene and the acyloxylating agent may be selected from a broad range of acid catalysts that are the same as those used in the decomposition of the diisopropylnaphthalene dihydroperoxide. Particularly preferred examples are inorganic acids such as sulfuric acid, hydrochloric acid, phosphoric acid and boron fluoride. Ion-exchange resins as solid acids may also be used. Bases may also be used as non-acid catalysts and besides organic bases such as pyridine and quinoline, sodium acetate and other salts may preferably be used. The amount of catalysts used varies with their type and the reaction conditions employed and it normally is preferable to use them in amounts ranging from 0.01 to 10 wt % of the total reaction mixture.

The reaction between the dihydroxynaphthalene and the acyloxylating agent such as a carboxylic acid anhydride is performed at a temperature in the range of 0°–200° C., preferably 80°–140° C. The reaction time ranges from about 30 minutes to about 5 hours, preferably from about 1 to about 2 hours.

As described above, an acyloxylating agent such as a carboxylic acid anhydride is added to the dihydroxynaphthalene-containing reaction product of acid decomposition and the dihydroxynaphthalene is reacted with the acyloxylating agent such as a carboxylic acid anhydride. Thereafter, the resulting reaction mixture is left to stand or otherwise cooled to obtain diacyloxynaphthalene as a precipitate from the reaction mixture.

The acyloxylation reaction may be performed on the acid decomposition product in the presence of a solvent such as an aromatic hydrocarbon (e.g. cumene), a dialkyl ketone (e.g., methyl isobutyl ketone) or a carboxylic acid. It is particularly preferable to perform the acyloxylation using methyl isobutyl ketone as the solvent because when the desired diacyloxynaphthalene is separated from the reaction mixture, the impurities remain in the latter as a result of extraction with the solvent, thereby allowing the diacyloxynaphthalene to be obtained with a higher purity.

The thus obtained diacyloxynaphthalene has a very high purity (>99%) and its yield is also very good, as high as 99% on a dihydroxynaphthalene basis. In addition, the recovery of diacyloxynaphthalene in crystal form is as high as 95 mol %.

EXAMPLES

The following examples are provided for the purpose of further illustrating the present invention but are in no way to be taken as limiting.

EXAMPLE 1

A 100-ml round-bottom flask equipped with a condenser pipe was charged with 2.0 g of 2,6-diacetoxynaphthalene, 20 g of methanol (solvent), 1.5 g of water and 0.12 g of conc. sulfuric acid (acid catalyst), and reaction was performed at 65° C. for 5 hours in a nitrogen atmosphere under stirring with a magnetic stirrer. Analysis of the reaction liquor by gas chromatography showed that 2,6-dihydroxynaphthalene had been produced in an amount of 5.5 wt % (yield, 99%) and 2,6-dihydroxynaphthalene dimer in an amount of 0.01 wt %.

EXAMPLE 2-5

The procedures of Example 1 were repeated except for the solvent and reaction temperature. The results are shown in Table 1.

COMPARATIVE EXAMPLE 1

The procedures of Example 1 were repeated except for the solvent and reaction temperature. The results are shown in Table 1.

TABLE 1

| Run | Solvent | Reaction temperature (°C.) | Yield of 2,6-dihydroxynaphthalene (wt %) |
|---|---|---|---|
| Example 2 | acetic acid | 80 | 98 |
| Example 3 | methyl acetate | 60 | 97 |
| Example 4 | dioxane | 80 | 97 |
| Example 5 | acetonitrile | 78 | 95 |
| Comparative Example 1 | methyl isobutyl ketone | 76 | 87 |

EXAMPLE 6

An apparatus of the same type as that used in Example 1 was charged with 2.0 g of 2,6-diacetoxynaphthalene, 20 g of methanol, 0.3 g of water and 0.12 g of conc. sulfuric acid, and reaction was performed at 65° C. for 5 hours with stirring in a nitrogen atmosphere. The yield of 2,6-dihydroxynaphthalene was 97%.

EXAMPLES 7 AND 8

The procedures of Example 6 were repeated except that conc. sulfuric acid was replaced by the catalysts shown in Table 2.

TABLE 2

| Run | Catalyst | Yield of 2,6-dihydroxynaphthalene (wt %) |
|---|---|---|
| Example 6 | sulfuric acid | 97 |
| Example 7 | hydrochloric acid | 95 |
| Example 8 | zinc chloride | 94 |

Comparative Example 2

The procedures of Example 6 were repeated except that conc. sulfuric acid was replaced by sodium hydroxide. Analysis of the reaction liquor by gas chromatography showed that 2,6-dihydroxynaphthalene had been produced in an amount of 4.9 wt % (yield, 84%) and 2,6-dihydroxynaphthalene dimer in an amount of 0.9 wt %.

INDUSTRIAL APPLICABILITY

In accordance with the process of the present invention, dihydroxynaphthalenes of high purity are obtained in high yield and the obtained dihydroxynaphthalenes of high purity are useful as starting materials in the production of synthetic resins, synthetic fibers, pharmaceuticals, agrichemicals, dyes, etc.

We claim:

1. A process for producing a dihydroxynaphthalene which comprises hydrolyzing a diacyloxynaphthalene in a water-containing solvent comprising water and a solvent selected from the group consisiting of alcohols, carboxylic acids, ketones, ethers and nitriles in the presence of an acid catalyst selected from the group consisting of inorganic acids, strong acidic ion-exchange resins, solid acids, organic acids and Lewis acids.

2. The process of claim I, wherein the diacyloxynaphthalene is a 2,6-diacycloxynaphthalene and, as a result, the dihydroxynaphthalene is 2,6-dihydroxynaphthalene.

3. The process of claim 1, wherein the said solvent used in highly miscible with water forming a homogeneous system under the reaction conditions.

4. The process of claim 1, wherein the said acid catalyst is used in an amount of 0.05 to 10 wt.% based on the reaction solvent.

5. The process of claim 1 wherein said solvent is an alcohol, and the amount of water in said water-containing solvent relative to diacyloxynaphthalene is in an amount of 2.0 or less in molar ratio.

6. The process of claim 1, wherein said solvent is selected from the group consisting of carboxylic acids, ketones, ethers and nitriles and wherein the amount of water in said water-containing solvent is in a molar ratio to diacyloxynaphthlene of at least 2.0.

7. The process of claim 6, wherein the amount of water in said water-containing solvent is in a molar ratio to diacyloxynaphthalene of at least 5.0.

8. The process of claim 7, wherein the amount of water in said water-containing solvent is in a molar ratio to diacyloxynaphthalene of at least 10.0.

9. The process of claim 1 wherein the diacyloxynaphthalene is hydrolyzed at a temperature of from 40° to 200° C.

10. The process of claim 1 wherein the diacyloxynaphthalene is hydrolyzed at a temperature of from 60° to 100° C.

11. The process of claim 1 wherein the acid catalyst is selected from the group consisting of sulfuric acid, hydrochloric acid, perchloric acid, hydrofluoric acid, strong acidic ion-exchange resins, silica, silica-alumina, chloroacetic acid, methanesulfonic acid, benzenesulfonic acid, toluenesulfonic acid, boron fluoride and zinc chloride.

12. The process of claim 11 wherein the acid catalyst is used in an amount of from 0.2 to 1.0 wt %, based on the reaction solvent.

13. The process of claim 1 wherein said solvent is selected from the group consisting of methanol, ethanol, isopropanol, ethylene glycol, formic acid, acetic acid, propionic acid, acetone, methylethyl ketone, dioxane carbitol and acetonitrile.

14. A process for producing highly pure 2,6-dihydronaphthalene, which comprises
  (i) hydrolyzing 2,6-diacetoxynaphthalene in a water-containing organic solvent comprising water and a solvent selected from the group consisting of alcohols, carboxylic acids, ketones, ethers and nitriles in the presence of an acid catalyst selected from the group consisting of inorganic acids, strong acidic ion-exchange resins, solid acids, organic acids and Lewis acids; and
  (ii) then separating produced 2,6-dihydroxynaphthalene from the reaction mixture.

15. The process of claim 14 wherein the reaction of step (i) carried out at a temperature of from 40° to 200° C.

16. The process of claim 14 wherein the reaction of step (i) is carried out at a temperature of from 60° to 100° C.

17. The process of claim 14 wherein the acid catalyst is selected from the group consisting of sulfuric acid, hydrochloric acid, perchloric acid, hydrofluroric acid, strong acidic ion-exchange resins, silica, silica-alumina, chloroacetic acid, methanesulfonic acid, benzenesulfonic acid, toluenesulfonic acid, boron fluroide and zinc chloride, and wherein the solvent is selected from the group consisting of methanol, ethanol, isopropanol, ethylene glycol, formic acid, acetic acid, propionic acid, acetone, methylethyl ketone, dioxane carbitol and acetonitrile.

* * * * *

UNITED STATES PATENT AND TRADEMARK OFFICE
CERTIFICATE OF CORRECTION

PATENT NO. : 4,962,241

DATED : October 9, 1990

INVENTOR(S) : Masaaki YASUDA and Hisaya MIKI

It is certified that error appears in the above-identified patent and that said Letters Patent is hereby corrected as shown below:

Column 1, line 11, change "hydroxymophthalenes" to --hydroxynaphthalenes--;

Column 1, line 23, change "2,6-dihydroynaphthalene" to
    --2,6-dihydroxynaphthalene--;

Column 1, line 26, change "2,6-dihydroxynaphthaelen" to
    --2,6-dihydroxynaphthalene--;

Column 2, line 65, insert a period (.) after "catalyst";

Column 3, line 10, change "tobuyloxy" to --tuluyloxy--;

Column 3, line 13, change "2,6-di hydroxynaphthalene" to
    --2,6-dihydroxynaphthalene--;

UNITED STATES PATENT AND TRADEMARK OFFICE
CERTIFICATE OF CORRECTION

PATENT NO. : 4,962,241

DATED : October 9, 1990

INVENTOR(S) : Masaaki YASUDA and Hisaya MIKI

It is certified that error appears in the above-identified patent and that said Letters Patent is hereby corrected as shown below:

Column 12, line 7, change "dronaphtalene" to --droxynaphthalene--.

Signed and Sealed this

Twenty-fourth Day of November, 1992

Attest:

DOUGLAS B. COMER

*Attesting Officer*  *Acting Commissioner of Patents and Trademarks*